United States Patent
Oliviero et al.

(10) Patent No.: US 9,238,027 B2
(45) Date of Patent: Jan. 19, 2016

(54) USE OF CB1 ANTAGONISTS AND/OR INVERSE AGONISTS FOR THE PREPARATION OF DRUGS THAT INCREASE MOTOR NEURON EXCITABILITY

(75) Inventors: Antonio Oliviero, Toledo (ES); Juan de los Reyes Aguilar Lepe, Toledo (ES); Mario Rotondi, Pavia (IT); Eduardo Molina Holgado, Toledo (ES); Luca Chiovato, Pavia (IT); Guglielmo Foffani, Madrid (ES); Laura Mordillo Mateos, Toledo (ES); Ángel Lozano Sicilia, Aranjuez (ES); Daniel García Ovejero, Madrid (ES); Ángel Arévalo Martín, Toledo (ES); Yolanda Pérez Borrego, Toledo (ES)

(73) Assignee: Fundacion del Hospital Nacional de Paraplejicos para la investigacion y la integracion (Fuhnpaiin), Toledo (ES)

( * ) Notice: Subject to any disclaimer, the term of this patent is extended or adjusted under 35 U.S.C. 154(b) by 442 days.

(21) Appl. No.: 13/144,078

(22) PCT Filed: Jan. 11, 2010

(86) PCT No.: PCT/ES2010/070012
§ 371 (c)(1),
(2), (4) Date: Oct. 4, 2011

(87) PCT Pub. No.: WO2010/079255
PCT Pub. Date: Jul. 15, 2010

(65) Prior Publication Data
US 2012/0015945 A1    Jan. 19, 2012

(30) Foreign Application Priority Data
Jan. 12, 2009  (WO) ............... PCT/ES2009/000010

(51) Int. Cl.
| A61K 31/5377 | (2006.01) |
| A61P 43/00 | (2006.01) |
| A61P 25/14 | (2006.01) |
| A61P 25/28 | (2006.01) |
| A61K 31/454 | (2006.01) |
| A61P 25/00 | (2006.01) |
| A61K 31/415 | (2006.01) |
| A61K 31/00 | (2006.01) |
| A61K 31/4164 | (2006.01) |

(52) U.S. Cl.
CPC ............. *A61K 31/415* (2013.01); *A61K 31/00* (2013.01); *A61K 31/4164* (2013.01); *A61K 31/454* (2013.01); *A61K 31/5377* (2013.01)

(58) Field of Classification Search
USPC ............................................. 514/236.5, 326
See application file for complete search history.

(56) References Cited

U.S. PATENT DOCUMENTS

| 5,596,106 A | 1/1997 | Cullinan et al. |
| 5,747,524 A | 5/1998 | Cullinan et al. |
| 6,017,919 A | 1/2000 | Inaba et al. |
| 6,028,084 A | 2/2000 | Barth et al. |
| 2001/0053788 A1 | 12/2001 | Lange et al. |
| 2003/0114495 A1 | 6/2003 | Finke et al. |
| 2005/0101585 A1* | 5/2005 | Antel et al. ............. 514/210.01 |
| 2008/0015228 A1 | 1/2008 | Bensaid et al. |
| 2008/0015229 A1 | 1/2008 | Hanotin et al. |
| 2008/0058381 A1 | 3/2008 | Piot-Grosjean et al. |
| 2008/0119653 A1 | 5/2008 | Vayron et al. |
| 2008/0200510 A1 | 8/2008 | Milosavljevic-Ristic |
| 2008/0221078 A1 | 9/2008 | Black et al. |
| 2009/0005361 A1 | 1/2009 | Webb |
| 2009/0124643 A1 | 5/2009 | Croci et al. |
| 2009/0215755 A1 | 8/2009 | Arnone et al. |
| 2009/0221692 A1 | 9/2009 | Grenard et al. |
| 2009/0239877 A1* | 9/2009 | Fehrentz et al. ......... 514/252.06 |
| 2009/0281143 A1 | 11/2009 | Nagy et al. |
| 2009/0306037 A1 | 12/2009 | Amatruda et al. |

FOREIGN PATENT DOCUMENTS

| EP | 0576357 | 6/1993 |
| EP | 0656354 | 11/1994 |
| EP | 0658546 | 12/1994 |

(Continued)

OTHER PUBLICATIONS

Hollander (Endocannabinoid Blockade for Improving Glycemic Control and Lipids in patients with Type 2 Diabetes Mellitus, the American Journal of Medicine (2007), vol. 120 (2A), S18-S28).*
Tyrrell (Fatigue after stroke, Therapy , 2005, 2(6), pp. 865-869).*
Weijman (Fatigue in employees with diabetes: its relation with work characteristics and diabetes related burden, Occup Environ Med, 2003, 60(Suppl 1), pp. i93-i98).*
Henness (Rimonabant, Drugs, 2006., 66 (16), pp. 2109-2119).*
Ward, "Functional reorganization of the cerebral motor system after stroke", Current Opinion in Neurology, 2004, 17, pp. 725-730.
Grasso et al., "La riabilitazione nelle lesioni nervose perferiche", La Clinica Terapeutica, 1997, 148, pp. 351-392.
Thickbroom et al., "Central motor drive and perception of effort during fatigue in multiple sclerosis", J. Neurol., 2006, 253, pp. 1048-1053.

(Continued)

*Primary Examiner* — Kathrien Cruz
(74) *Attorney, Agent, or Firm* — Buchanan Ingersoll & Rooney PC

(57) ABSTRACT

Use of a CB1 receptor antagonist and/or inverse agonist, preferably rimonabant, for the preparation of drugs useful for increasing motor neuron excitability in the cerebral cortex and/or in the brain stem and/or at the spinal level, as well as a method for increasing motor neuron excitability through the administration of a CB1 antagonist/inverse agonist receptors, and to the use of a pharmaceutical composition which comprises a CB1 receptor antagonist and/or inverse agonist, preferably rimonabant, for increasing motor neuron excitability in the cerebral cortex and/or in the brain stem and/or at the spinal level.

4 Claims, 3 Drawing Sheets

(56) References Cited

FOREIGN PATENT DOCUMENTS

| | | |
|---|---|---|
| EP | 0969835 | 7/1998 |
| EP | 1150961 | 11/2001 |
| EP | 1328269 | 7/2003 |
| EP | 1446384 | 8/2004 |
| WO | 99/00119 | 1/1999 |
| WO | 01/29007 | 4/2001 |
| WO | 0170700 | 9/2001 |
| WO | 02/28346 | 4/2002 |
| WO | 02076949 | 10/2002 |
| WO | 03/007887 | 1/2003 |
| WO | 03026647 | 4/2003 |
| WO | 03026648 | 4/2003 |
| WO | 03027076 | 4/2003 |
| WO | 03051851 | 6/2003 |
| WO | 03078413 | 9/2003 |
| WO | 03/082256 | 10/2003 |
| WO | 2004026301 | 4/2004 |
| WO | 2005020988 | 3/2005 |
| WO | 2005028456 | 3/2005 |
| WO | 2005040130 | 5/2005 |
| WO | 2005047285 | 5/2005 |
| WO | 2005049615 | 6/2005 |

OTHER PUBLICATIONS

Gandevia, "Spinal and Supraspinal Factors in Human Muscle Fatigue", Physiological Reviews, 2001, vol. 81, No. 4, pp. 1725-1790, downloaded from physrev.physiology.org on Nov. 9, 2011.

Oliviero et al., "Functional involvement of cerbral cortex in human narcolepsy", J. Neurol., 2005, 252, pp. 56-61.

Gennaro et al., "Neurophysiologcial correlates of sleepiness: A combined TMS and EEG study", NeuroImage, 2007, 33, pp. 1277-1287.

Wu et al., "Noninvasive Brain Stimulation for Parkinson's Disease and Dystonia", Neurotherapeutics: The Journal fo the American Society for Experimental NeuroTherapeutics, 2008, vol. 5, pp. 345-361.

Rinaldi-Carmona, et al., "SR147116A, a potent and selective antagonist of the brain cannabinoid receptor", FEBS Letters, 1994, 350, pp. 240-244.

Pertwee, "The pharmacology of cannabinoid receptors and their ligands: an overview", International Journal of Obesity, 2006, 30, pp. S13-S18.

Hosohata, et al., "AM630 is a Competitive Cannabinoid Receptor Antagonist in the Guinea Pig Brain", Life Sciences, 1997, vol. 61, No. 9, pp. 115-118.

Felder et al., "LY320135, a Novel Cannabinoid CB1 Receptor Antagonist, Unmasks Coupling of the CB1 Receptor to Stimulation of cAMP Accumulation", The Journal of Pharmacology and Experimental Therapeutics, 1998, 284, pp. 291-297.

Kanyonyo, et al., 3-Alkyl-(5,5'-Diphenyl)Imidazolidinediones As New Cannabinoid Receptor Ligands, Bioorganic & Medicinal Chemistry Letters, 1999, 9, pp. 2233-2236.

Landsman, et al., "SR141716A is an inverse agonist at the human cannabinoid CB1 receptor", European Journal of Pharmacology, 1997, 334, pp. R1-R2.

Mechoulam, et al., "Endocannabinoids", European Journal of Pharmacology, 1998, 359, pp. 1-18.

Hallett, "Transcranial magnetic stimulation and the human brain", Nature, 2000, vol. 406, pp. 147-150.

Perio, et al., "Central mediation of the cannabinoid cue: activity of a selective CB1 antagonist, SR 141716A", Behavioural Pharmacology, 1996, 7, pp. 65-71.

Pertwee, "Cannabinoid receptor ligands: clinical and neuropharmacological considerations, relevant to future drug discovery and development", Exp. Opin. Invest. Drugs, 2000, 9(7), pp. 1553-1571.

Kujirai, et al., "Corticocortical Inhibition in Human Motor Cortex", Journal of Physiology, 1993, 471, pp. 501-519, downloaded from J. Physiol (jp.physoc.org) on Nov. 9, 2011.

2011 Annual Meeting, 2011 Neuroscience Meeting Planner, Washington, DC: Society for Neuroscience, 2011, pp. 1-1337.

Felder, et al., "Comparison of the Pharmacology and Signal Transduction of the Human Cannabinoid CB1, and CB2 Receptors", Modular Pharmacology, 1996, 48, pp. 443-450.

Hillard, et al., "Synthesis and Characterization of Potent and Selective Agonists of the Neuronal Cannabinoid Receptor (CB1)", The Journal of Pharmacology and Experimental Therapeutics, 1999, 289, pp. 1427-1433.

Dickenson, et al., "Pain Relief", IDrugs, 1999, 2(11), pp. 1130-1132.

Barth, "Cannabinoid receptor agonists and antagonists", Exp . Opin. Ther. Patents, 1998, 8(3), pp. 301-313.

Di Marzo et al., "A Structure/Activity Relationship Study on Arvanil, an Endocannabinoid and Vanilloid Hybrid", The Journal of Pharmacology and Experimental Therapeutics, 2002, 300, pp. 984-991.

* cited by examiner

USE OF CB1 ANTAGONISTS AND/OR INVERSE AGONISTS FOR THE PREPARATION OF DRUGS THAT INCREASE MOTOR NEURON EXCITABILITY

CROSS REFERENCE TO RELATED APPLICATIONS

This application is a national phase of PCT/ES2010/070012 filed on Jan. 11, 2010 which claims priority to PCT/ES2009/000010 filed on Jan. 12, 2009, the entire disclosures of all of which are incorporated by reference herein.

The invention relates to the use of a CB1 receptor antagonist and/or inverse agonist, preferably rimonabant, for the preparation of drugs useful for increasing motor neuron excitability in the cerebral cortex and/or in the brain stem and/or at the spinal level, as well as a method for increasing motor neuron excitability through the administration of a CB1 receptor antagonist/inverse agonist, and to the use of a pharmaceutical composition which comprises a CB1 receptor antagonist and/or inverse agonist, preferably rimonabant, for increasing motor neuron excitability in the cerebral cortex and/or in the brain stem and/or at the spinal level. Therefore, the present invention belongs to the field of invention of medicine.

PRIOR ART

The endogenous cannabinoid system is formed by endogenous ligands, their synthesis and degradation enzymes and by two different specific receptors cloned to date: cannabinoid receptor type 1 (CB1), and cannabinoid receptor type 2 (CB2). The agonists of the cannabinoid receptor type 1 (CB1) may reduce spasticity and pain in a great number of neurological, rheumatic, traumatic diseases and in cancer. The agonism of the CB1 receptor also causes sleepiness.

Rimonabant is the inn (International nonproprietary name) for N-(piperidin-1-yl)-5-(4-chlorophenyl)-1-(2,4-dichlorophenyl)-4-methyl-1H-pyrazole-3-carboxamide. This compound was described for the first time in EP 656354 as a CB1 receptor antagonist/inverse agonist. Rimonabant has passed several clinical trials where it was proposed as a new alternative to treat obesity, achieving the marketing authorization of several medicine agencies including the European Medicines Agency (EMEA), and it was marketed in the European Union as ACOMPLIA®. With this indication, ACOMPLIA®, which comprises a dose of 20 mg/day of rimonabant, was used as a supplement for diet and exercise in treating obese patients (defined as BMI+30 Kg/m$^2$ (BMI=body mass index)), or patients with BMI>27 kilograms/m$^2$ which also have risk factors associated, such as type 2 diabetes or dyslipidemia. Due to the continuous revisions medical science undergoes, the Committee for Medical Products of Human Use (CHMP) decided to restrict the use of the drug after July 2007. The CHMP recommended a new updating of the use of Acomplia® in May 2008 and in October 2008, it concluded that the benefits of Acomplia® for this indication did not compensate the risks observed and it decided to suspend the marketing authorization of the drug for the whole of the European Union (EU).

However, until now the capacity of Acomplia® for increasing motor neuron excitability and its effects on fatigue had not been determined, which extends the use of CB1 antagonists/inverse agonists as active components in the treatment of a large number of medical disorders.

Many neurological pathologies are characterized by a decrease in cortical and spinal motor neuron excitability and more generally by a decrease in corticospinal motor output (for example, cerebral vasculopathies, spinal cord injury, chronic fatigue syndrome, etc). It is also necessary to highlight that some diseases that are not characterized by a decrease in motor neuron excitability benefit from a temporary increase in motor neuron excitability and an increase in corticospinal motor output (for example, peripheral nerve pathologies, muscular hypotrophies, muscular fatigue, etc). In all these clinical conditions, an increase in motor neuron excitability and consequent increase in corticospinal output is beneficial. At present there are no treatments of proven efficacy for increasing motor neuron excitability and the consequent corticospinal output.

Many neurological pathologies are characterized by excessive sleepiness (hypersomnia, narcolepsy, chronic fatigue syndrome, Parkinson's disease. etc). In all these clinical conditions an increased activity of the arousal system is beneficial. At the present time there are few treatments of proven efficacy to activate the arousal system.

There are currently no treatments of proven efficacy for any of the disease related to movement disorders that have symptoms that can be beneficially treated by increasing the motor neuron excitability.

DESCRIPTION OF THE INVENTION

The present inventors have surprisingly found that CB1 receptor antagonists and/or inverse agonists increase motor neuron excitability in the cerebral cortex, the brain stem and at the spinal level in human patients. The present inventors have also surprisingly found that CB1 receptor antagonists and/or inverse agonists increase the activity of the ascending activation system or arousal system. The present invention also discloses treatments for diseases related to a decrease in motor neuron excitability and/or the decrease in activation of the ascending activation system or arousal system, i.e. it relates to the use of the CB1 receptor antagonist and/or inverse agonist for the preparation of a drug for the treatment of diseases where the increase in motor neuron excitability in the cerebral cortex, the brain stem and/or at the spinal level is beneficial.

Therefore, the object of the present invention is the use of a CB1 receptor antagonist and/or inverse agonist for the preparation of a drug for the treatment of movement disorders, fatigue, the reduction of excessive daytime sleepiness, the reduction of bradykinesia and/or the reduction of hypokinesia.

DESCRIPTION OF THE FIGURES

In FIG. 1 the baseline values are shown in black and the values after rimonabant administration in white. The administration of rimonabant significantly reduced the mean of the active motor threshold using transcranial magnetic stimulation, hereinafter called AMTtms (baseline 39±4% vs 35.5±4%; P=0.0008) whilst the resting motor threshold value using transcranial magnetic stimulation, hereinafter called RMT was not significantly affected (baseline 48±6% vs. 46.5±6% P=0.0775).

The administration of rimonabant significantly reduced the mean of the active motor threshold using transcranial electric stimulation, hereinafter called AMTtes (baseline 19.6±6% vs 17.5±6%; P=0.0164).

Figure 1:
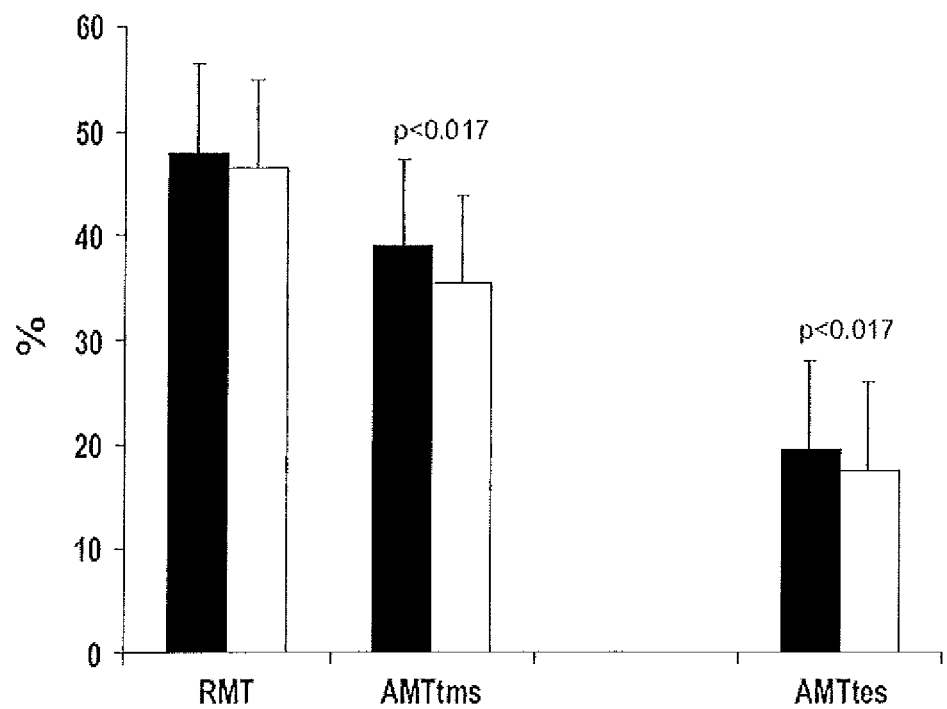
FIG. 1 shows the threshold values using transcranial magnetic and electric stimulation before and after administration of 20 mg of rimonabant. The threshold value is expressed in percentage (%) of the maximum stimulator output. The error bars represent the standard deviations.
Figure 2:
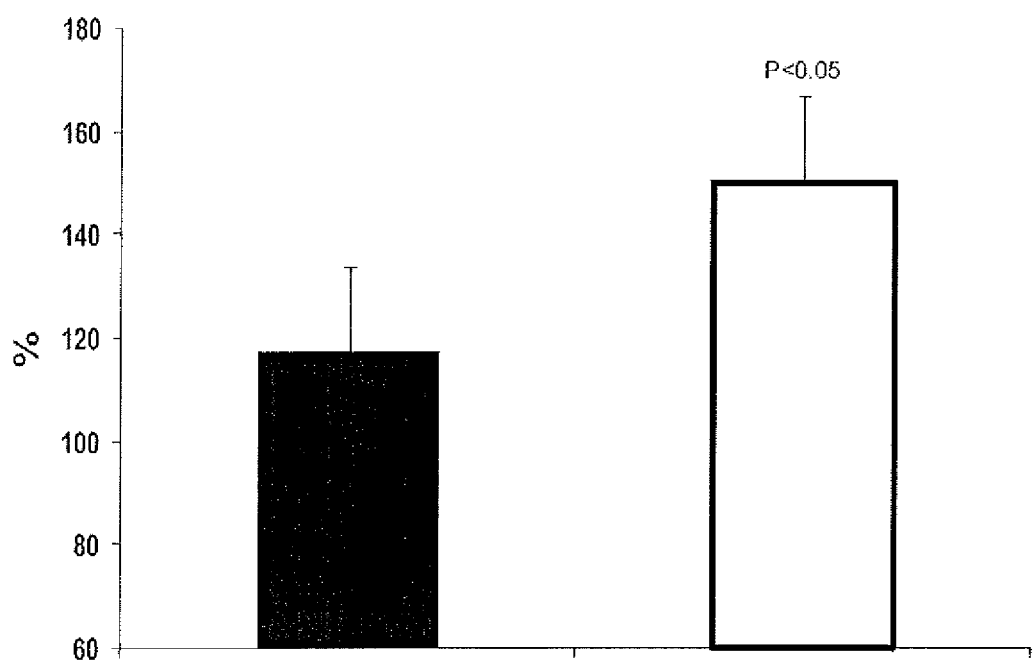

FIG. 2 shows the amount of intracortical facilitation (ICF) before and after administration of 20 mg of rimonabant. The ICF value is expressed in percentage (%) of the response obtained with the stimulation test in absence of the conditioning stimulus. The error bars represent the standard deviations. In FIG. 2 the baseline values are shown in black and the values after rimonabant administration in white. The administration of rimonabant significantly increased the mean of ICF (baseline 117±21% vs+150±40%; P=0.0212).

Figure 3:
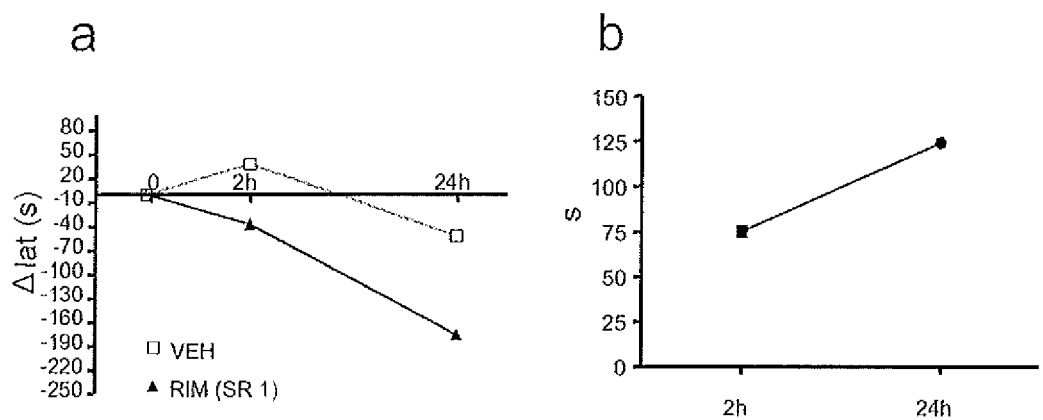

FIG. 3 shows that the treatment of rats with CB1 receptor antagonists/inverse agonists (SR141716A in this example) decreased latency in the 24 hours after the injection, which means that inhibition of this receptor increased resistance to fatigue during that time (FIG. 3a). This effect can clearly be observed in FIG. 3b, which shows that the improvement in resistance to fatigue (decrease in latency) of the rats treated with CB1 receptor antagonists/inverse agonists (SR141716A in this example) was on average 75 seconds better in animals with SR141716A than in the animals treated with carrier 2 hours after fatigue; and 125 seconds better in the animals with SR141716A than in the animals treated with carrier 24 hours after fatigue. The X-axis indicates the time in hours (h) and the Y-axis indicates the Δ of the latency in seconds (a) and the improvement in seconds with respect to the carrier (b).

Figure 4:
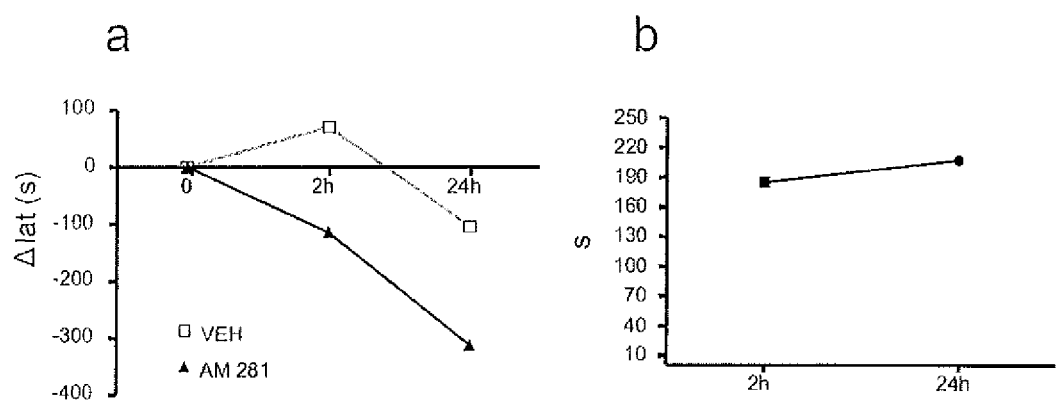

FIG. 4 shows that the treatment of rats with CB1 receptor antagonists/inverse agonists (AM281 in this example) decreased latency in the 24 hours after injection, which means that the inhibition of this receptor increased resistance to fatigue during that time (FIG. 4a). This effect can clearly be observed in FIG. 4b, which shows that the improvement in resistance to fatigue (decrease in latency) of the rats treated with CB1 receptor antagonists/inverse agonists (AM281 in this example) was on average 185 seconds better in animals with AM281 than in the animals treated with carrier 2 hours after fatigue; and 207 seconds better in the animals with AM281 than in the animals treated with carrier 24 hours after fatigue. The X-axis indicates the time in hours (h) and the Y-axis indicates the Δ of the latency in seconds (a) and the improvement in seconds with respect to the carrier (b).

Figure 5:
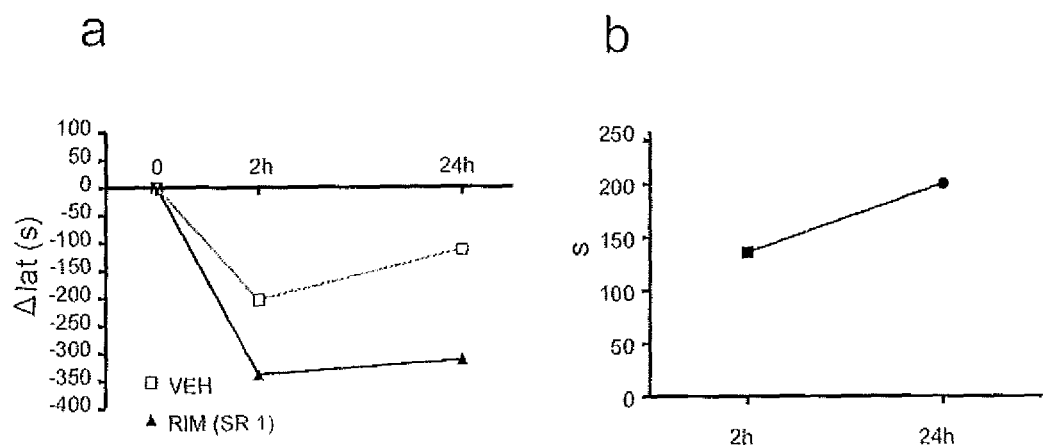

FIG. 5 shows that CB1 receptor antagonists/inverse agonists increase resistance in rats with moderate spinal cord injury subjected to forced run. As was observed for normal rats, the treatment of injured rats with rimonabant (SR141716A) decreased latency, i.e. it increased resistance to fatigue 2 hours after the injection compared to the carriers (FIG. 5a). At the time of completing the fatigue test, 24 h later, the performance of the carrier rats and SR141716A maintained the differences observed on the previous day (FIG. 5a). This effect can be clearly observed in FIG. 5b, which shows that the improvement in resistance to fatigue (decrease in latency) of the rats treated with CB1 receptor antagonists/ inverse agonists (SR141716A in this example) was on average 136 seconds better in the animals with SR141716A than in the animals treated with carrier 2 hours after fatigue; and 200 seconds better in the animals with SR141716A than in the animals treated with carrier 24 hours after fatigue. The X-axis indicates the time in hours (h) and the Y-axis indicates the Δ of the latency in seconds (a) and the improvement in seconds with respect to the carrier (b).

DETAILED DESCRIPTION OF THE INVENTION

The surprising effect of CB1 receptor antagonists and/or inverse agonists of increasing motor neuron excitability at the cortical level and/or in the brain stem and/or at the spinal level can be used to treat diseases or pathologies related to movement disorders and/or the recovery of motor function in central nervous system diseases characterized by motor dysfunction, such as strokes, multiple sclerosis or spinal cord lesion. All these pathologies are characterized by having a decrease in corticospinal motor output and/or a decrease in motor neuron excitability (Ward, Curr Opin Neurol. 2004 December, 17(6), 725-30, Thickbroom et al., J. Neurol. 2006 August, 253(8), 1048-53). For this reason, an increase in corticospinal motor output and/or increase in motor neuron excitability is beneficial. The effect of increasing motor neuron excitability at the cortical level, in the brain stem and/or at the spinal level may be accompanied by exercise or rehabilitation to encourage motor recovery. In a particular embodiment the movement disorder related to the central nervous system is strokes, in another embodiment it is multiple sclerosis, and a third embodiment it relates to use for the treatment of spinal cord lesions.

The use of CB1 receptor antagonists and/or inverse agonists is not limited to movement disorders of the central nervous system, but they are also useful for the treatment of movement disorders related to the peripheral nervous system, such as, for example, peripheral paralysis. The rehabilitation of these nerve lesions benefits from greater activation of the altered nerve (see Grasso et al., Clin Ter. 1997 September, 148(9), 351-92). An increase in motor neuron excitability produces a greater activation of the nerve and, therefore, is beneficial.

When motor neuron excitability is increased at the cortical level, in the brain stem and/or at the spinal level, it may allow or improve the recovery of motor function in those diseases characterized by motor dysfunction caused by disorders of the peripheral nervous system, such as neuropathies of the cranial nerves (e.g. facial) and spinal nerve (e.g. Bell's palsy, Guillain-Barré syndrome, motor and sensorial-motor neuropathies). The effect of increasing motor neuron excitability at the cortical level, in the brain stem and/or at the spinal level may be accompanied with exercise or rehabilitation to encourage motor recovery. The rehabilitation of these nerve lesions benefits from greater activation of the altered nerve (see Grasso et al., Clin Ter. 1997 September, 148(9), 351-92). An increase in motor neuron excitability produces a greater activation of the nerve and, therefore, is beneficial.

In a preferred embodiment, said disease of the peripheral nervous system is motor neuropathy of the cranial and spinal nerves.

In another preferred embodiment, said disease of the peripheral nervous system is Bell's palsy.

In a preferred embodiment, said disease of the peripheral nervous system is Guillain-Barré syndrome.

Fatigue is a decrease in the capacity to voluntarily produce maximum muscular force. Fatigue occurs in numerous parts of the motor pathway, including motor neurons, motor cortex and the spinal cord. Fatigue is caused by different central and peripheral nervous mechanisms. Fatigue is characterized by a decrease in cortical and spinal motor neuron excitability (Thickbroom et al., J. Neurol. 2006 August, 253(8), 1048-53; Gandevia, Physiol Rev. 2001 October, 81(4), 1725-89) and by the decrease in cortical motor output (Gandevia, Physiol Rev. 2001 October, 81(4), 1725-89). An increase in motor neuron excitability and the consequent increase in cortical motor output are beneficial. The present inventors have found that the CB1 receptor antagonists and/or inverse agonist reduce the feeling of fatigue, in particular of fatigue associated to strokes, multiple sclerosis and/or chronic fatigue syndrome. In a preferred embodiment said disease characterized by excessive fatigue is strokes. In another preferred embodiment said disease characterized by excessive fatigue is multiple sclerosis. And in another preferred embodiment said disease characterized by excessive fatigue is chronic fatigue syndrome.

Another particular embodiment relates to the use of CB1 receptor antagonists and/or inverse agonists for the treatment of motor neuron dysfunction.

The increase in motor neuron excitability at the cortical level, in the brain stem and/or at the spinal level can be used to temporarily improve function in motor neuron disorders such as amyotrophic lateral sclerosis and primary lateral sclerosis. In a preferred embodiment said disease is amyotrophic lateral sclerosis. In a preferred embodiment said disease is primary lateral sclerosis.

The increase in activity of the arousal systems can be used to reduce excessive daytime sleepiness which leads to narcolepsy and sleep disorders characterized by hypersomnia. Narcolepsy is characterized by a reduction in cortical excitability (Oliviero et al., J. Neurol. January 2005, 252 (1), 56-61) whereby the increase in this excitability leads to a reduction thereof. The possibility of increasing the activity of the arousal systems is beneficial for excessive daytime sleepiness and hypersomnia associated to a decrease in the activity of the arousal systems and which is also present with a decrease in cortical motor neuron excitability (By Gennaro et al., Neuroimage. 2007 Jul. 15, 36(4), 1277-87).

The increase in motor neuron excitability at the cortical level, in the brain stem and/or at the spinal level, can be used for the treatment of bradykinesia and/or hypokinesia (e.g. Parkinson's disease and Parkinsonisms). The symptoms of Parkinson's disease and Parkinsonisms improve when, using non-pharmacological neuromodulation techniques, the excitability of the cerebral cortex is increased (see Wu et al., Neurotherapeutics. 2008 April, 5(2), 345-61). An increase in motor neuron excitability, and the consequent increase in cortical motor output, is beneficial in Parkinson's disease and in Parkinsonisms.

An additional particular object of the invention is a method to improve normal motor function and/or accelerating recovery after a lesion of any origin (vascular, inflammatory, traumatic, etc.) of the central nervous system and/or peripheral nervous system and/or muscular system. The rehabilitation of these nervous lesions benefits from greater activation of the altered motor functions (see Grasso et al., Clin Ter. 1997 September, 148(9), 351-92). An increase in motor neuron excitability produces greater functional activation of the motor function and, therefore, may be beneficial. Another object of the present invention is the use of a composition which comprises a CB1 receptor antagonist and/or inverse agonist to improve training in athletes. The training of athletes benefits from a greater activation of the motor functions, for which reason the increase in motor neuron excitability is beneficial as it produces greater motor activation (see Lehmann et al., J Sports Med Phys Fitness. 1997 March, 37(1), 7-17).

The advantages of the present invention are associated to the cannabinoid receptors present at the cortical level and/or in the brain stem and/or at the spinal level, for which reason the surprising effects of the present invention are applicable to all CB1 antagonists and/or inverse agonists. The term "CB1 antagonist" designates an antagonist of the cannabinoid CB1 receptor. This is a compound which bonds to the receptor and lacks substantial capacity to activate the receptor of same. An antagonist prevents or reduces functional activation or the occupation of the receptor by an agonist, such as anandamide. In some embodiments, the antagonist has an $IC_{50}$ of around 1 µM to around 1 nM. In other embodiments, the antagonist has an $IC_{50}$ of around 0.1 µM to 0.01 µM, 1.0 µM M to 0.1 µM, or to 0.01 per µM to 1 nm. In some embodiments, the antagonist competes with the agonist in bonding to a shared bonding site in the receptor. These compounds are very well known and highly defined in the state of the art. For example, U.S. Pat. No. 5,747,524 and U.S. Pat. No. 6,017,919 disclose some of the valid methods for screening activity to CB1, which makes it possible to identify the compounds useful in the invention.

In the classic activation model of G-protein coupled receptors, the classic two-stage model, the agonist ligands stabilize or increase the fraction of active receptor, so that it can interact and activate a G-protein signal transducer and subsequent effectors. The ligands called inverse agonists stabilize or increase the fraction of inactive receptor, whilst the neutral antagonists do not alter the balance between the active or inactive states of the receptor. The first generation of cannabinoid receptor antagonists developed in the 1990s, such as, for example SR141716A, a selective ligand for CB1 (Rinaldi-Carmona et al., FEBS Lett. 1994 Aug. 22; 350(2-3):240-4), LY320135 or molecules designed by Alexandros Makriyannis: AM251 and AM281 which are analogues to SR141716A, produce opposite effects to those of CB1 agonists. These inverse cannabinomimetic effects occur in the absence of endogenous cannabinoids, which suggested that the cannabinoid CB1 receptors could exist in a state of constitutive activation in the absence of an agonist ligand, so that the inverse agonists displace the active state of the receptor to an inactive state. The inverse agonists produce opposite effects to those of the agonists in some of the receptor bioassays. For example, "in vivo" the inverse agonism includes the signs of hyperalgia in inflammatory or neuropathic pain models (formalin test), carrageenan-induced paw oedema, the stimulation of intestinal motility, or the suppression of food consumption, whilst "in vitro" it produces an increase in neurotransmitter release (acetylcholine, noradrenaline or gamma aminobutyric) or inhibition of the bonding of [$^{35}$S] GTPγS in membrane preparations (see Pertwee R G in International Journal of Obesity 2006, 30, S13-S18)

A first group of cannabinoid CB1 receptor antagonists are pyrazole derivatives. Patents EP 576357 and EP 658546 disclose examples of pyrazole derivatives with affinity for the cannabinoid receptors. More particularly, patent EP 656354 shows examples of pyrazole derivatives and discloses the compound N-piperidin-5-(4-chlorophenyl)-1-(2,4-dichlorophenyl)-4-methylpyrazole-3-carboxamide, or SR 141716, and its pharmaceutically acceptable salts, which have good affinity for central cannabinoid receptors.

Another additional example of CB1 receptor antagonist is shown in U.S. Pat. No. 5,596,106, which discloses the compounds arylbenzo[b]thiophene and benzo[b]furane as inhibitors or blockers of cannabinoid receptors in mammals.

Preferably, the cannabinoid antagonist is selective of the CB1 receptor and has a $IC_{50}$ with respect to the CB1 receptor which is a fourth part or less than the $IC_{50}$ for the CB2 receptor, or more preferably a tenth part or less of the $IC_{50}$ of the CB2 receptor, and even more preferably a one hundredth part of the $IC_{50}$ of CB2 receptors.

Each of the aforementioned references is included for reference in its totality.

Another representative example is iodopravadoline (AM-630). AM-630 is a CB1 receptor antagonist, but sometimes behaves as weak partial agonist (Hosohata, K.; Quock, R. M.; Hosohata, Y.; Burkey, T. H.; Makriyannis, A.; Consroe, P.; Roeske, W. R.; Yamamura, H. I. Life Sc. 1997, 61, PL115). More recently, the researchers of Eli Lilly described arylaroyls substituting benzofuranes as CB1 receptor antagonists (e.g. LY-320135) (Felder, C. C.; Joyce, K. E.; Briley, E. J.; Glass, M.; Mackie, K. P.; Fahey, K. J.; Cullinan, G. J.;

Hunden, D. C.; Johnson, D. W.; Chaney, M. O.; Koppel, G. A.; Brownstein, M. J. Pharmacol. Exp. Ther. 1998, 284, 291). Recently, 3-alkyl-(5,5'-diphenyl)imidazolidinediones were described as ligands of cannabinoid receptors which indicated that they were cannabinoid receptor antagonists (Kanyonyo, M., Govaerts, S. J.; Hermans, E.; Poupaert, J. H., Lambert, D. M. Biorg. Med. Chem. Lett. 1999, 9, 2233).

Surprisingly, many CB1 receptor antagonists have been described with behaviour of inverse agonists in vitro (Landsman, R. S.; Burkey, T. H.; Consroe, P.; Roeske, W. R.; Yamamura, H. I. Eur. J. Pharmacol. 1997, 334, R1). Recent reviews provide a good description of the current state of the art in the area of research into cannabinoids (Mechoulam, R.; Hanus, L.; Fride, E. Prog. Med. Chem. 1998, 35, 199. Lambert, b. M. Curr. Med. Chem. 1999, 6, 635. Mechoulam, R.; Fride, E.; Di Marzo, V. Eur. J. Pharmacol. 1998, 359, 1).

WO 01/70700 discloses the potent and selective antagonist activity on CB1 receptors of 4,5-dihydro-1H-pyrazole compounds.

The compounds of the following formula are also useful as cannabinoid CB1 receptors:

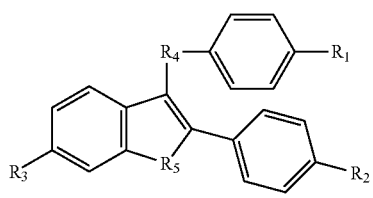

Where the substituents $R_1$, $R_2$, $R_3$, $R_4$, and $R_5$ are defined in U.S. Pat. No. 5,596,106 which is incorporated for reference in its totality. This reference discloses additional examples of derivatives of aryl-benzo[b]thiophenes and arylbenzo[b]furanes and their use in accordance with the present invention.

The cannabinoid antagonists with the following formula are particularly useful in accordance with the present invention.

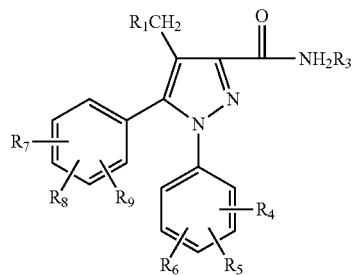

Where $R_1$ is hydrogen, a fluoride, a hydroxyl, a $(C_1-C_5)$ alkoxy, a $(C_1-C_5)$thioalkyl, a hydroxyl$(C_1-C_5)$alkoxy, a $—NR_{10}R_{11}$ group, a cyano, a $(C_1-C_5)$alkylsulfonyl or a $(C_1-C_5)$ alkylsulfinyl; $R_2$ and $R_3$ are independently a $(C_1-C_4)$alkyl or, they form a heterocyclic radical of 5 to 10 members together with nitrogen whereto they are bonded which is not substituted or which is monosubstituted or polysubstituted by a $(C_1-C_3)$alkyl or by a $(C_1-C_3)$alkoxy; $R_4$, $R_5$, $R_6$, $R_7$, $R_8$ and $R_9$ are independently hydrogen, halogen or trifluoromethyl, and if $R_1$ is a fluoride, $R_4$, $R_5$, $R_6$, $R_7$, $R_8$ and/or $R_9$ can also be a fluoromethyl, with the condition that at least one of the $R_4$ or $R_7$ substituents is another substituent that is not hydrogen; and $R_{10}$ and $R_{11}$ are independently hydrogen or a $(C_1-C_5)$ alkyl, or $R_{10}$ and $R_{11}$, together with nitrogen whereto they are bonded form a heterocyclic radical selected from among pyrrolidin-1-yl, piperidin-1-yl, morpholin-4-yl and piperazine-1-yl, which are or are not substituted by a $(C_1-C_4)$alkyl, and its salts and solvates.

Other selective examples of CB1 antagonist compounds are useful in the context of the present invention including (but not being limited to):

1) Analogue diarylpyrazoles described by Sanofi as selective CB1 antagonists, as a representative example are the compounds SR-141716A, SR-147778, SR-140098, rimonabant and related compounds disclosed in patents EP 0969835 and EP 1150961 (Central mediation of the cannabinoid cue: activity of a selective CB1 antagonist, SR 141716A Perio A, Rinaldi-Carmona M, Maruani J Behavioural Pharmacology 1996, 7:1 (65-71)); WIN-54461 described by Sanofi-Winthrop (Cannabinoid receptor ligands: Clinical and neuropharmacological considerations relevant to future drug discovery and development. Pertwee R G, Expert Opinion on Investigational Drugs 1996, 5:10 (1245-1253)).

N-piperidin-5-(4-chlorophenyl)-1-(2,4-dichlorophenyl)-4-methylpyrazole-3-carboxamide (SR 141616, CAS number: 168273-06-1), and its pharmaceutically acceptable salts and its solvates have been usefully described in the preparation of drugs for the treatment of appetite disorders.

SR 141716, (inn: rimonabant) is represented by the formula:

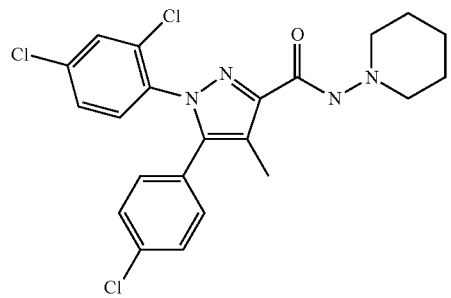 [SMILES: Cc1c(C(=O)NN2CCCCC2)nn(-c2ccc(Cl)cc2Cl)c1-c1ccc(Cl)cc1]

Rimonabant is especially described in patent EP 656354 or in the article by M. Rinaldi-Carmona et al. (FEBS Lett., 1994, 350, 240-244). Patent EP1446384 A1 discloses new rimonabant derivatives, the formulation which comprises rimonabant is disclosed in WO2003082256, and the use of rimonabant in appetite disorders is disclosed in patent WO99/00119.

2) Aminoalkylindoles have been described as CB1 receptor antagonists. A representative example is the compound Iodopravadoline (AM-630).

3) Aryl-aroyl substitute the benzofuranes described by Eli Lilly as selective CB1 antagonists receptors, e.g. LY-320135 (Cannabinoid receptor ligands: Clinical and neuropharmacological considerations relevant to future drug discovery and development. Pertwee R G, Expert Opinion on Investigational Drugs 1996, 5:10-(1245-1253)).

4) The compounds described by Merck & Co, e.g. AM 251 and AM 281 (Conference: 31st Annual Meeting of the Society for Neuroscience, San Diego, USA, 10-15, November 2001), and the substituted imidazolyl derivatives described in, e.g. US 2003114495 or WO 03/007887.

5) The azetidine derivatives described by Aventis Pharma, for example, in patent WO 02/28346 or in EP 1328269.

6) CP-55940 from Pfizer Inc. (Comparison of the pharmacology and signal transduction of the human cannabinoid CB1 and CB2 receptors, Felder C C, Joyce K E, Briley E M, Mansouri J, Mackie K, Blond O, Lai Y, Ma A L, Mitchell R L, Molecular Pharmacology 1995, 48, 3 (443)).

7) The diaryl-pyrazine-amide derivatives from Astra Zeneca described, for example, in patent WO 03/051851.

8) ACPA and ACEA from Med. Coll. Wisconsin (Univ. Aberdeen), ("Effects of AM 251 & AM 281, cannabinoid CB1 antagonists, on palatable food intake in lewis rats" J. Pharmacol. Exp. Ther. 289, No 3, 1427-33, 1999).

9) The pyrazole derivatives described by the University of Connecticut e.g. in patent WO 01/29007.

10) HU-210 (International Association for the Study of Pain-Ninth World Congress (Part II) Vienna, Austria, Dickenson A H, Carpenter K, Suzuki R, IDDB MEETING REPORT 1999, Aug. 22-27) and HU-243 (Cannabinoid receptor agonists and antagonists, Barth F, Current Opinion in Therapeutic Patents 1998, 8, 3 (301-313)) from the Yissum R&D Co Hebrew Univ. of Jerusalem.

11) O-823 from Organix Inc. (Drug development pipeline: O-585, O-823, O-689, O-1072, monamines, Orgaix, Altropane Organix Inc, Company Communication 1999, Aug. 10; IDDb database) and O-2093 from the Consiglio Nazionale delle Ricerche ("A structure/activity relationship study on arvanil, endocannabinoid and vanilloid hybrid.", Marzo D V, Griffin G, Petrocellis L, Brandi I, Bisogno T, Journal of Pharmacology and Experimental Therapeutics 2002, 300, 3 (984-991)).

12) The 3-alkyl-(5,5'-diphenyl)imidazolidinediones described as cannabinoid receptor ligands.

13) The CB1 antagonist compounds currently under development by Bayer AG (IDDb database: company communication 2002, Feb. 28).

14) The CB1 antagonist pyrazole derivatives in accordance with formula (I) of U.S. Pat. No. 6,028,084 incorporated for reference in its totality.

15) U.S. Pat. No. 6,017,919 discloses another appropriate group of cannabinoid receptor antagonists and their use in accordance with the present invention, with general formula:

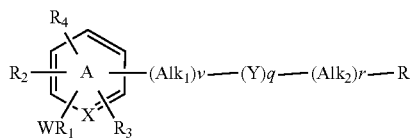

Where the substituents are defined in U.S. Pat. No. 6,017,919 which is incorporated for reference in its totality.

16) The antagonist activity in CB1 receptors of 4,5,dihydro-1H-pyrazole derivatives was shown in U.S. Pat. No. 5,747,524 and in US 2001/0053788 A1, published on 20 Dec. 2001.

17) The 4,5,dihydro-1H-pyrazole derivative with CB1 receptor antagonist activity disclosed in patent US 2001/0053788A1 and particularly described by formula (I) contained in the aforementioned patent, published on 20 Dec. 2001 and which is incorporated for reference in its totality.

18) The CB1 receptor antagonists disclosed in patent WO 2005049615 especially the compounds described in examples 1 to 8.

19) The CB1 receptor antagonists disclosed in patent application WO 2005047285 especially the compounds described in examples 1 to 99.

20) The CB1 receptor antagonist (4R)-3-(4-chlorophenyl)-4,5-dihydro-N-methyl-4-phenyl-N'-[[4-(trifluoromethyl)phenyl]sulfonyl]-1H-pyrazole-1-carboximidamide (SLV 326-34th Neuroscience, Abs 1009.4, October 2004) developed by Solvay (WO 0170700 A1).

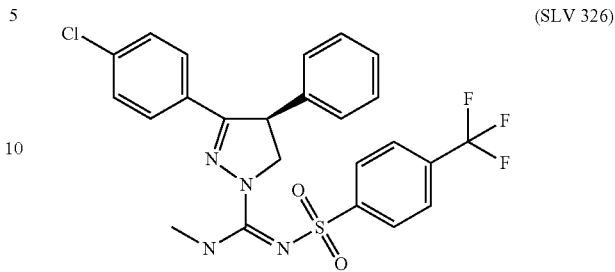

(SLV 326)

The CB1 receptor antagonists developed by Solvay are described in the examples of the following patents: WO 2005040130 A1, WO 2005028456 A1, WO 2005020988 A1, WO 2004026301 A1, WO 2003078413 A1, WO 2003027076 A2, WO 2003026648 A1, WO 2003026647 A1, WO 2002076949 A1 and WO 0170700 A1.

Particularly preferred are the CB1 receptor antagonists selected from the group consisting of rimonabant, AM-630, AM251, AM281, LY-320135, HU-210, HU-243, O-823, O-2093, SLV 326 and SR147778, preferably rimonabant, AM251 or SR147778, more preferably rimonabant; and according to the case its pharmaceutically acceptable salts.

Below, some patient applications are listed wherein CB1 antagonists and/or inverse agonists are disclosed: US 2008015228, US 2008015229, US 2008058381, US 2008119653, US 2008200510, US 2008221078, US 2009005361, US 2009124643, US 2009215755, US 2009221692, US 2009281143 and US 2009306037.

Some of the substances previously cited in scientific documents, patents or by reference to other patents and their potential classes are considered potentially useful for the embodiments of the present invention, for which reason their content is fully incorporated in the present application for reference.

In another particular embodiment the CB1 receptor antagonist and/or inverse agonist comprises the following substructure and any of its tautomers and/or pharmaceutically acceptable salts:

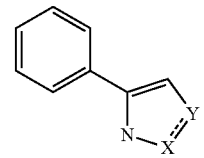

With X and Y being independently selected from carbon and nitrogen. Especially preferred are the substructures that in the phenyl ring are substituted by at least one halogen group, preferably Cl, Br or I, and more preferably in the para position.

Below, we list a series of particular CB1 receptor antagonists and/or inverse agonists useful for the present invention, whether in the form of free base or pharmaceutically acceptable salt:

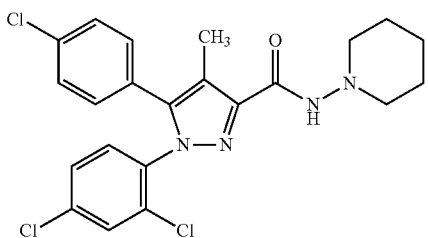

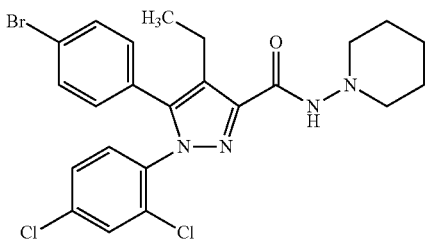

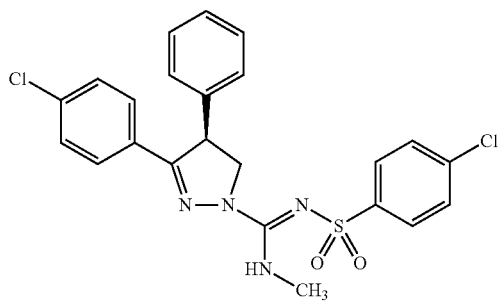

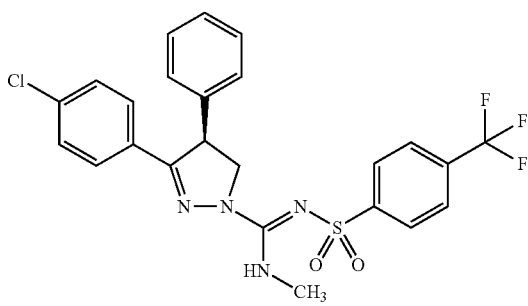

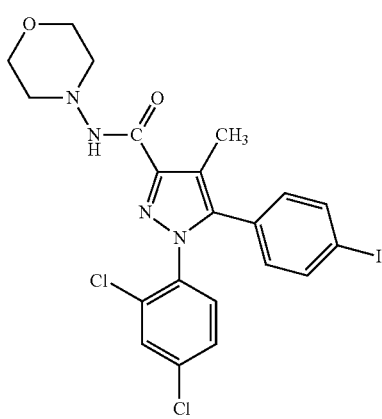

AM281

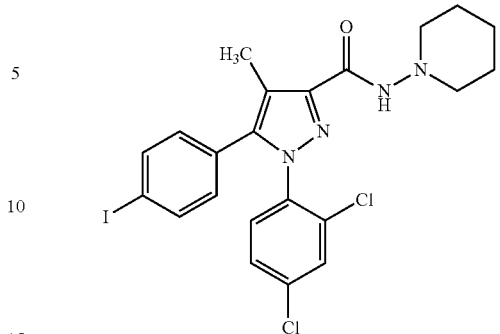

AM251

The term "pharmaceutically acceptable salts" relates to a non-toxic salt of common use in the pharmaceutical industry which can be prepared in accordance with methods well-known in the state of the art. The preferred salts for the compounds of the invention are those formed by HCl, HBr, HI, H2SO4, oxalic acid and benzoic acid.

The term "treatment" is understood to be the management and care of a patient in order to fight against the disease or disorder.

The compounds of the invention are administered at a therapeutically effective dose. The term "therapeutically effective" relates to a quantity of a drug or therapeutic agent which causes the desired biological response of a tissue, a system or an animal (including man) which is being sought by a researcher or clinic.

The dose of CB1 antagonist and/or inverse agonist shall depend on the health of the subject treated, and the desired extension of the treatment, the nature and the type of therapy, the frequency of treatment and the nature of the effect desired. In general, the dose of the agent is in the range of around 0.001 to around 50 mg/kg in weight of patient per day, preferably expressed in daily dose per human patient between 1 and 2000 mg/day and even more preferably between 5 and 500 mg, administered in a single dose or divided. However, a certain variability in the dose range may also be necessary depending on the age, weight and type of patient, also depending on the planned administration route and how advanced it is and degree of severity of the disease or condition.

An indicative daily dose is in the range of between 1 and 500 mg, preferably from 1 to 100 mg of active agent, especially when it is for oral use. The dose can be administered in one go or in divided doses. Preferably, the CB1 antagonists and/or inverse agonists are administered in the suitable form of unit dose, for example, a capsule or tablet, and which comprises a therapeutically effective dose, for example of around 2 to around 200 mg. The active principle may be applied up to three times a day, preferably one or two times a day. The same recommended dose is selected for the fixed combinations. The daily dose of rimonabant required in the practice of the method of the present invention may vary depending on, for example, the form of administration and the severity of the disease to be treated. A daily dose of rimonabant is indicated in the range of between 1 to around 100 mg, preferably between 5 and 40 mg or 5 and 20 mg, of active agent of oral use, appropriately administered in one go or in divided doses. Preferably rimonabant is administered in the form of pharmaceutical composition comprising at least one pharmaceutically acceptable excipient this oral composition preferably being in the form or oral solid, such as, for example capsules or granules.

The administration of the effective quantity may be performed in different manners such as, for example, oral, sublingual, subcutaneous, intramuscular, intravenous, topical, local, intratracheal, intranasal, transdermal and rectal administration. The most preferred form of pharmaceutical composition is oral and solid, preferably in the form of capsules or tablets.

Preferably, the CB1 antagonist or inverse agonist is administered in the form of pharmaceutical composition which comprises between 1 and 2000 mg of CB1 receptor antagonist and/or inverse agonist and at least one pharmaceutically acceptable excipient or carrier, preferably between 5 and 500 mg.

The term "pharmaceutically acceptable excipient" is understood to be any ingredient which does not have therapeutic activity and which are not toxic and, therefore, are suitable as excipient. Suitable excipients include the excipients of common use of pharmaceutical products such as, for example, microcrystalline cellulose, lactose, starch, magnesium stearate, crosspovidone, povidone and talc.

EXAMPLES

Example 1

Motor Neuron Excitability

The following experiments were performed using rimonabant, but it should be understood that in no way should the scope of the present invention be limited to the example proposed below. In contrast, that tested for rimonabant can be extended to other CB1 antagonists or inverse agonists.

Rimonabant, a CB1 receptor antagonist, penetrates the hematoencephalic barrier and it is well known that, at the doses normally used (20 mg per day), produces psychological effects in healthy human beings with a wide range of symptoms.

The objective of the present experiments was to use transcranial magnetic and electric stimulation to test the effects of a single dose of 20 mg of rimonabant in motor cortex and spinal motor neuron excitability.

A neurophysiological examination was carried out before and 24 hours after administration of a single dose of 20 mg of rimonabant.

Using transcranial magnetic stimulation (TMS) we evaluate the electromyographic response thresholds in the first dorsal interosseous (FDI) at rest and during voluntary contraction. Using transcranial electric stimulation (TES) we evaluate the electromyographic response thresholds in the first dorsal interosseous during voluntary contraction. Transcranial electric stimulation tends to activate the axons of the corticospinal neurons in the white matter whilst magnetic stimulation activates the same fibres trans-synaptically (Hallett, 2000 Jul. 13, 406 (6792):147-50). Therefore, the response evoked electrically are not as sensitive to changes in cortical excitability as those evoked by magnetic stimulation. We also evaluate short-latency intracortical facilitation (ICF). ICF was studied using the technique of Kujirai et al. (J. Physiol. 1993 November; 471:501-19).

Two magnetic stimuli were applied with the same stimulation coil, using a Bistim module (Magstim Co., Whitland, UK) on the motor cortex and the effect was studied of the first stimulus (conditioning factor) on the second stimulus (test). The conditioning stimulus was set at an intensity of 90% of the threshold under activation.

The intensity of the stimulus tests was adjusted to evoke a motor evoked potential (MEP) at rest in the FDI with an amplitude of, approximately, 1 mV from peak to peak. The programming of the conditioning stimulus was altered in relation to the test stimulus. The interstimulus intervals (ISIs) of 10, 15 and 25 ms were then investigated. Five stimuli were applied in each ISI.

The response facilitation conditional upon the three different ISIs studied was then averaged to give a magnified average value. The amplitude of the motor evoked potentials was expressed as percentages of amplitude of the motor evoked potentials of the tests. The ICF is a form of facilitation of the corticospinal pathways which occurs at the cortical level.

Subjects

Nine healthy volunteers (average age±S.D 32.1±5.8 years) participated in the experiments using TMS (transcranial magnetic stimulation) and six participated in the experiments with electric stimulation. All subjects gave their informed written consent. The study was developed in accordance with the Declaration of Helsinki and approved by the Local Ethics Committee. The magnetic stimulation was developed using two Magstim 200 high-power magnetic stimulators (Magstim Co., Whitland, UK) connected to the Bistim Module during all measurements. A figure of 8 shaped coil was placed with an external diameter of 9 cm on the right motor cortex, in optimal position of the head to provoke a motor response in the contralateral first dorsal interosseous. The current induced a flow in the posteroanterior direction. The rest motor threshold (RMT) was defined as the stimulus of minimum intensity capable of producing a motor evoked response at rest (of around 50 µV in 50% of the 10 attempts). The active motor threshold (AMTtms) was defined as the stimulus of minimum intensity capable of producing a motor evoked response (around 200 µV in 50% of the 10 attempts) during the isometric contraction of the muscle tested at approximately 20% of the maximum. A constant voluntary contraction level was maintained by electromyogram display oscilloscope placed in front of the subject.

In six subjects we also performed electric stimulation of the motor cortex during voluntary contraction. This was performed with a Digitimer D180A digital stimulator with a time constant of 50 µs. The cathode was placed in the vertex and the anode at 7 cm laterally (anodic stimulation). We evaluate the active electric motor threshold (AMTtes) defined as the stimulus of minimum intensity capable of producing a motor evoked response of around 200 µV in 50% of ten attempts during the voluntary contraction. The effects of rimonabant on attention were moderate and did not interfere with the capacity of subjects to completely comply with the experimental protocol requirements. Three of the subjects experienced agitation and anxiety (this effect lasted an average of 6 hours) and one suffered nauseas (during 24 h).

The RMT, the AMTtms and the AMTtes were compared before and after taking rimonabant using a paired t-test applying the Bonferroni correction (0.05/3=0.017). The ICF was compared before and after rimonabant using a paired t-test.

The administration of rimonabant significantly reduced the average of AMTtms (baseline 39±4% vs 35.5±4%; P=0.0008) whilst the RMT was not affected (baseline 48±6% vs 46.5±6% P=0.0775).

The administration of rimonabant significantly reduced the average of AMTtes (baseline 19.6±6% vs 17.5±6%; P=0.0164). The administration of rimonabant significantly increased the average of ICF (baseline 117±21% vs +150±40%; P=0.0212).

Rimonabant reduced AMTtms and AMTtes but did not have effects on the rest motor threshold.

RMT and AMTtms reflect the excitability properties of the corticospinal neurons intrinsically and extrinsically modulated (Hallett, 2000). At the cortical level, AMTtms reflect the activity of a descending wave: the I1 wave (Di Lazzaro et al., Clin Neurophysiol. 1998, 109 (5):397-401). But also a change in the excitability of the spinal motor neuron may affect the AMTtms. Basing ourselves on these considerations, we have demonstrated that the I1 waves or spinal cord motor neurons are facilitated by the rimonabant CB1 antagonism/inverse agonism.

Transcranial electric stimulation tends to activate the axons of the corticospinal neurons in the white matter whilst magnetic stimulation activates the same fibres trans-synaptically (Hallett, 2000 Jul. 13, 406 (6792):147-50). Therefore, the responses evoked electrically are not as sensitive to changes in cortical excitability as those evoked by magnetic stimulation.

Therefore, an effect similar to rimonabant in the electromyographic responses evoked by magnetic and electric stimulation demonstrates that the increase in excitability takes place—perhaps not exclusively—in the spinal cord circuits. The present result provides the first evidence that the excitability of the spinal motor circuits, verified by transcranial magnetic and electric stimulation circuits, may be increased by blocking CB1 receptors using rimonabant. However, it is difficult to exclude a cortical role in the presence of changes in excitability of the motor circuits at the spinal level only using threshold studies by transcranial stimulation.

Another important observation is that rimonabant increases intracortical facilitation. ICF occurs at the cortical level (Hallett, 2000 Jul. 13, 406(6792): 147-50) for which reason we can conclude that the results present provide the first evidence that cortical motor neuron excitability may be increased in humans by blocking CB1 using rimonabant.

Example 2

Fatigue

The objective of this study consisted of determining the effects of cannabinoid CB1 receptor antagonists/inverse agonists (Rimonabant—SR141716A—, AM281) on fatigue in rats produced by a conveyer belt.
Material and Methods Animals. Male adult Wistar rats were used (300-350 g; 12 weeks old), obtained from Harlan-Interfauna Ibérica (Barcelona, Spain) kept in our animal house in a light:dark cycle of 12:12 hours, receiving food and water ad libitum. The animals were handled in accordance with the guides published in the "NIH Guide for the Care and Use of Laboratory Animals", the principles covered by the "Guidelines for the Use of Animals in Neuroscience Research" published by the American Neuroscience Society, and the European Union Guidelines (Directive 86/609/EEC). The rats were assigned to the groups with injection of carrier or the CB1 antagonists/inverse agonists (rimonabant (SR141716A) or AM281). Five uninjured animals and 3 injured animals were used for each group.

Forced Run Protocol Using the Conveyer Belt and Treatments.

The rats were acclimatized to the conveyer belt making them walk on the belt at low speed. The forced run protocol consisted of a first session of 15 minutes run (20 m/min, 5% inclination) followed by a second session 2 hours later (Fatigue 2 h). The same protocol was repeated the following day to study the continuance of the effects observed with the treatment (Fatigue 24 h). In order to keep the rats running throughout the study, mild electric shock was used (20 mV, 1.67 Hz) and, possible, gentle touches by the experimenter's hand. The drugs were administered immediately after the first session of the first day. The treatments consisted of a single intraperitoneal injection of SR141716A (0.25 mg/Kg), or AM281 (0.25 mg/Kg), or carrier (2.5% Bovine Serum Albumin, SIGMA, Spain, in 0.9% NaCl).

Latency was defined as the number of seconds during the experiment where the animals touched the grille located at the end of the conveyer belt. The animals that remained more than twice at the electric grille receiving discharges of over 10 seconds were considered exhausted and were returned to their cages. In this case, latency time was also considered the remaining time until the end of the protocol. The latency increase (Δ latency) was calculated as the difference between the action of the rat at each time minus the values of the first session. Therefore, the negative measurements reflect a decrease in latency, and, therefore, an improvement in motor capacity.
Results The CB1 receptor antagonists/inverse agonists increase resistance in rats subjected to a forced run.

The treatment of rats with CB1 receptor antagonists/inverse agonists (SR141716A or AM281) decreased latency 2 hours after the injection, which means that the inhibition of this receptor increased resistance to fatigue in that time. On the following day, in the second measurement of the fatigue test, the rats treated with carrier performed the task in a similar manner to the previous day whilst in the groups with CB1 receptor antagonists/inverse agonists (SR141716A or AM281), not only was the improvement observed in the resistance maintained but it was increased above the levels of the previous day (FIGS. 3a and 4a). This effect can clearly be observed in FIGS. 3b and 4b, showing the improvement in resistance to fatigue (decrease in latency) of the rats treated with CB1 receptor antagonists/inverse agonists (SR141716A, AM281) was on average 75 and 185 seconds better in animals with SR141716A or AM281 than in the carrier 2 hours after fatigue; and 125 and 207 seconds better in animals with SR141716A or AM281 than in the carrier 24 hours after fatigue.

Example 3

Moderate Spinal Cord Lesion

The objective of this study consisted of determining the effects of cannabinoid CB1 receptor antagonists/inverse agonists (Rimonabant—SR141716A) in rats with moderate medullary lesion on the locomotion and fatigue produced by conveyer belt.
Material and Methods 6 animals were subjected to a moderate spinal cord lesion by, using the "Infinite Horizon" motorized system (Precision Systems & Instrumentation, [PSI], Lexington, Ky.). The animals were anaesthetized with an intraperitoneal injection of pentobarbital sodium (45 mg/kg, Normon Veterinary Division, Madrid, Spain) and Xilagesic (2% Xylazine, 10 mg/kg, Calier, Barcelona, Spain). When an absence of reflexes were observed, the rats were injected with a low dose of atropine (50 µg/kg of body weight; Brown Medical, Barcelona, Spain) to reduce salivary and bronchial secretion, and to avoid the presence of bradycardia and a possible cardiac arrest caused by surgery or by xylazine. Artificial tears were applied in the eyes to prevent corneal abrasion and infection. After removing the spinal crest of the eighth thoracic vertebra, the spinal column of the animal was stabilized with clips and the lesion was performed with a computer-controlled striker, which hits the surface of the spinal cord with a force of 150 Kdyn. After closing the lesion site, the animals were hydrated and were placed in hot blankets during one hour. Post-operatory care included a subcutaneous injection of Buprex (Buprenorphine, 0.05 mg/kg; Schering Plough, Madrid, Spain) and the prophylactic injection of antibiotic 1 hour after the lesion and on the following day (Baytril, Enrofloxacine, 1 mg/kg; Bayer, Kiel, Germany). The animals were fed with food for extruded rodents and the bladder was manually emptied until autonomous control of the emptying was recovered. The hydration state was monitored as was the presence of possible infections in the animals until the end of the experiment. The experiments with conveyer belt were performed 7 days after the lesion.

Modified Protocol for Forced Run on the Conveyer Belt for Those Injured Rats

As the spinal cord lesion produced clear deficits in the animals' locomotion, the fatigue protocol was modified to adapt it: Keeping the same strategy of two sessions per day, we change the conveyer belt settings, forcing the run more progressively and more prolonged. In this way, the rats were subjected to a rate of 10 m/min during 10 minutes, 15 m/min during 5 minutes, and, finally, 20 m/min during another 5 minutes (always with a 5° inclination). The drugs were administered as in the other non-injured groups.

Results

The CB1 receptor antagonists/inverse agonists increase resistance in rats with spinal cord lesion subjected to a forced run.

As was observed for normal rats, the treatment of injured rats with rimonabant decreased latency, i.e. it increased the resistance to fatigue 2 hours after the injection compared with the carriers (average of 136 seconds difference in favour of the animals treated with SR141716A; FIG. 5). At the time of completing the fatigue test, 24 h later, the performance of the carrier rats and SR141716A maintained the differences observed the previous day (average of 200 seconds difference in favour of the animals treated with SR141716A; FIG. 5).

The invention claimed is:

1. A method for the treatment of fatigue associated with stroke comprising administering to a patient in need thereof an effective amount of a CB1 receptor antagonist and/or inverse agonist, wherein said CB1 receptor antagonist and/or inverse agonist is selected from the list consisting of rimonabant and a compound of the following formula:

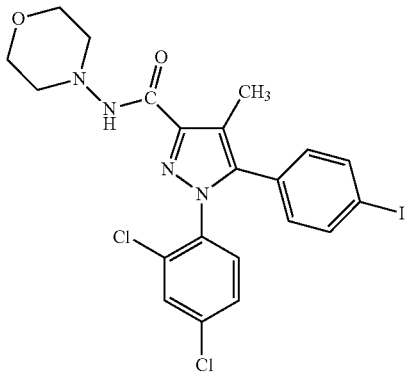

AM281 or any of its pharmaceutically acceptable salts.

2. The method according to claim 1, characterized in that the CB1 receptor antagonist and/or inverse agonist comprises rimonabant.

3. The method of claim 2, wherein the fatigue is associated with stroke.

4. The method of claim 1, wherein the fatigue is associated with stroke.

* * * * *